United States Patent [19]

Wang

[11] Patent Number: 5,515,478
[45] Date of Patent: May 7, 1996

[54] AUTOMATED ENDOSCOPE SYSTEM FOR OPTIMAL POSITIONING

[75] Inventor: Yulun Wang, Goleta, Calif.

[73] Assignee: Computer Motion, Inc., Goleta, Calif.

[21] Appl. No.: 305,415

[22] Filed: Sep. 13, 1994

Related U.S. Application Data

[63] Continuation of Ser. No. 927,801, Aug. 10, 1992, abandoned.

[51] Int. Cl.$^6$ .............................. A61B 1/00; A61C 19/04
[52] U.S. Cl. .............................. 395/86; 395/80; 395/92; 395/94; 395/97; 395/924; 364/413.02; 364/413.13; 128/774; 606/19; 606/46
[58] Field of Search .................. 395/86, 92, 80, 395/94, 97, 924; 364/413.02, 413.13; 128/4, 6, 774; 606/19, 46

[56] References Cited

U.S. PATENT DOCUMENTS

| | | | |
|---|---|---|---|
| 4,221,997 | 9/1980 | Flemming | 395/80 |
| 4,456,961 | 6/1984 | Price et al. | 364/191 |
| 4,474,174 | 10/1984 | Petruzzi | 128/4 |
| 4,517,963 | 5/1985 | Michel | 128/6 |
| 4,655,257 | 4/1987 | Iwashita | 138/120 |
| 4,676,243 | 6/1987 | Clayman | 606/180 |
| 4,728,974 | 3/1988 | Nio et al. | 901/44 |
| 4,791,934 | 12/1988 | Brunnett | 128/653 |
| 4,794,912 | 1/1989 | Lia | 128/4 |
| 4,815,006 | 3/1989 | Anderson et al. | 395/86 |
| 4,854,301 | 8/1989 | Nakajima | 128/4 |
| 4,930,494 | 6/1990 | Takehana et al. | 128/4 |
| 4,979,949 | 12/1990 | Matsen, III et al. | 395/80 |
| 4,996,975 | 3/1991 | Nakamura | 128/6 |
| 5,020,001 | 5/1991 | Yamamoto et al. | 395/86 |
| 5,065,741 | 11/1991 | Uchiyama et al. | 128/24 EL |
| 5,078,140 | 1/1992 | Kwoh | 901/41 |
| 5,086,401 | 2/1992 | Glassman et al. | 395/93 |
| 5,142,930 | 9/1992 | Allen et al. | 901/47 |
| 5,184,601 | 2/1993 | Putman | 395/94 |
| 5,217,003 | 6/1993 | Wilk | 128/4 |
| 5,228,429 | 7/1993 | Hatano | 901/9 |
| 5,230,623 | 7/1993 | Guthrie et al. | 433/72 |
| 5,251,127 | 10/1993 | Raab | 364/413.13 |
| 5,271,384 | 12/1993 | McEwen et al. | 128/20 |
| 5,279,309 | 1/1994 | Taylor et al. | 128/782 |
| 5,339,799 | 8/1994 | Kami et al. | 128/4 |
| 5,402,801 | 4/1995 | Taylor | 128/6 |
| 5,417,210 | 5/1995 | Funda et al. | 128/4 |

FOREIGN PATENT DOCUMENTS

| | | |
|---|---|---|
| 0239409 | 9/1987 | European Pat. Off. . |
| 924118 U | 7/1992 | Germany . |
| WO91/04711 | 4/1991 | WIPO . |

OTHER PUBLICATIONS

Fu et al, "Robotics: Control, Sensing, Vision and Intelligence" McGraw–Hill Book Company, 1987.

*Primary Examiner*—George B. Davis
*Attorney, Agent, or Firm*—Blakely, Sokoloff Taylor & Zafman

[57] ABSTRACT

A robotic system that moves a surgical instrument in response to the actuation of a foot pedal that can be operated by the foot of a surgeon. The robotic system has an end effector that is adapted to hold a surgical instrument such as an endoscope. The end effector is coupled to a robotic arm assembly which can move the endoscope relative to the patient. The system includes a computer which controls the movement of the robotic arm in response to input signals received from the foot pedal.

7 Claims, 4 Drawing Sheets

AUTOMATED ENDOSCOPE SYSTEM FOR OPTIMAL POSITIONING

This is a continuation of application Ser. No. 07/927,801 filed Aug. 10, 1992, now abandoned.

BACKGROUND OF THE INVENTION

1. Field of the Invention

The present invention relates to a robotic system for remotely controlling the position of a surgical instrument.

2. Description of Related Art

Endoscopes typically contain a lens that is coupled to a visual display by a fiber optic cable. Such a system allows the user to remotely view an image in front of the scope. Endoscopes are commonly used in a surgical procedure known as laparoscopy, which involves inserting the endoscope into the patient through a small incision in the abdomen. The endoscope allows the surgeon to internally view the patient without being in a direct line of sight with the object. The use of an endoscope typically reduces the size of the incision needed to perform a surgical procedure.

Endoscopes are commonly used to assist the surgeon in removing the gall bladder of a patient. Because the surgeon typically requires both hands to remove a gall bladder, the endoscope must be held and operated by a assistant. During the surgical procedure, the surgeon must frequently instruct the assistant to move the endoscope within the patient. Such a method can be time consuming as the surgeon may have to relay a series of instructions until the assistant has positioned the endoscope in the proper location. Additionally, the assistant may be unable to consistently hold the instrument in a fixed position, resulting in a moving image. This is particularly true for surgical procedures that extend over a long period of time.

There is presently a system marketed by Leonard Medical Inc. which mechanically holds an endoscope. The Leonard Medical system is an articulated mechanism which has a plurality of pneumatically powered joints that hold the endoscope in a fixed position. To move the endoscope, the pneumatic powered joints must be initially released into a relaxed condition. The surgeon or assistant then moves the scope and reactivates the pneumatic system. Although the Leonard system holds the endoscope in one position, the system requires the surgeon or assistant to constantly deactivate/activate the pneumatics and manually move the scope. Such a system interrupts the surgery process and increases the time of the surgical procedure. It would be desirable to provide a system that allows the surgeon to directly and efficiently control the movement of an endoscope.

SUMMARY OF THE INVENTION

The present invention is a robotic system that moves a surgical instrument in response to the actuation of a foot pedal that can be operated by the foot of a surgeon. The robotic system has an end effector that is adapted to hold a surgical instrument such as an endoscope. The end effector is coupled to a robotic arm assembly which can move the endoscope relative to the patient. The system includes a computer which controls the movement of the robotic arm in response to input signals from the foot pedal.

The computer computes the amount of incremental movement required to move the end effector in accordance with a set of algorithms. The algorithms transform the input of the foot pedal so that the movement of the endoscope as seen by the surgeon is always in the same direction as the movement of the foot pedal. Thus when the foot pedal is depressed to move the endoscope up or down, the end effector is manipulated so that the scope always moves relative to the image in an up or down direction as viewed by the surgeon.

Therefore it is an object of the present invention to provide a system which allows a surgeon to remotely control the position of a surgical instrument.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
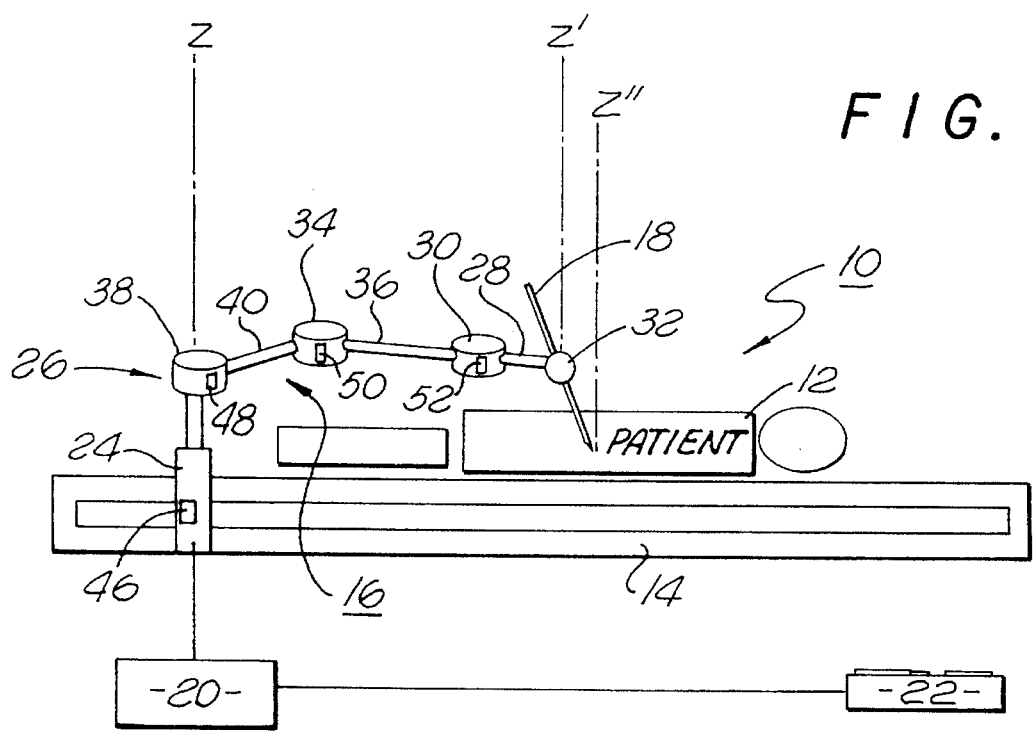
FIG. 1 is a side view of a robotic system of the present invention.
Figure 2:
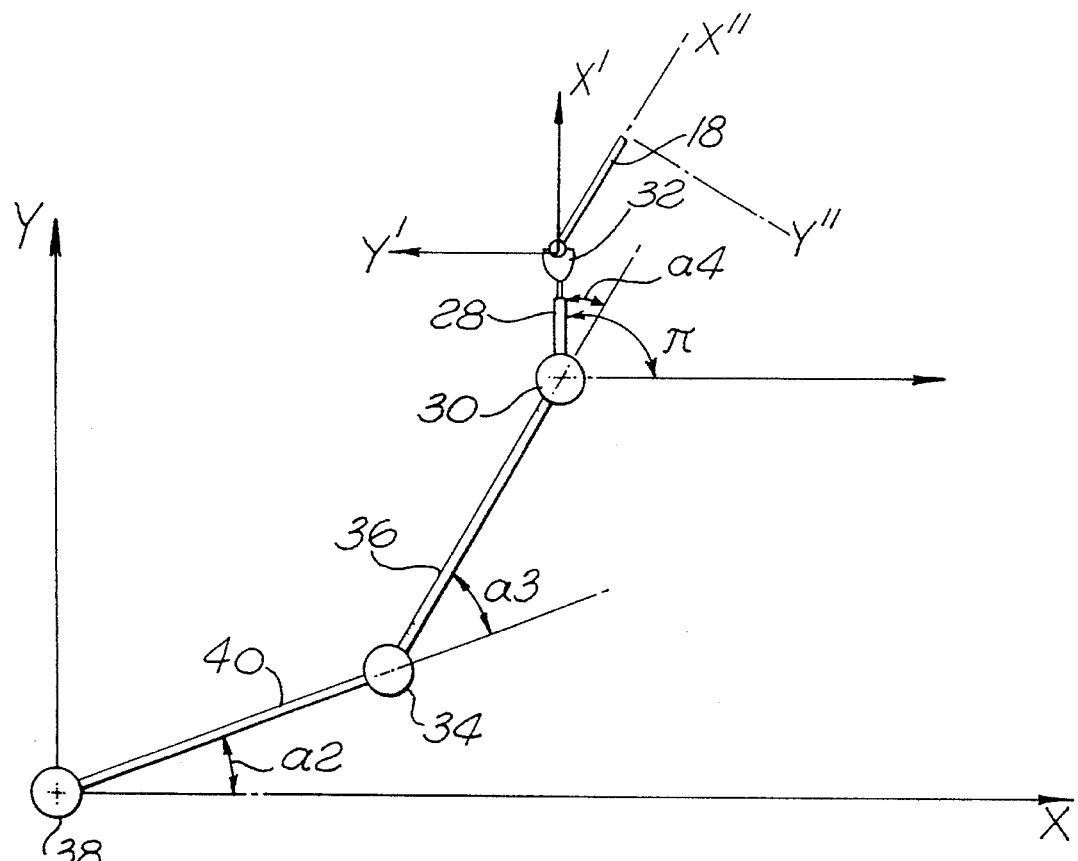
FIG. 2 is a top view of the robotic system of FIG. 1.

Referring to the drawings more particularly by reference numbers, FIGS. 1 and 2 show a robotic system 10 of the present invention. The system 10 is typically used in a sterile operating room where a surgeon (not shown) performs a surgical procedure on a patient 12. The patient 12 is placed on a operating table 14. Attached to the table 14 is a robotic arm assembly 16 which can move a surgical instrument 18 relative to the table 14 and the patient 12. The surgical instrument 18 is typically an endoscope which is inserted into the abdomen of the patient 12. The endoscope 18 enters the patient through cannula, wherein the scope 18 rotate about a cannula pivot point. The endoscope is typically connected to a display screen (not shown) which allows the surgeon to view the organs, etc. of the patient. Although an endoscope is described and shown, it is to be understood that the present invention can be used with other surgical instruments.

The system 10 has a computer 20 that is connected to the robotic arm assembly 16 and a foot pedal 22. The foot pedal 22 is located in close proximity to the operating table 14, so that the surgeon can operate the foot pedal 22 while performing a surgical procedure. The system 10 is constructed so that the surgeon can move the surgical instrument 18 by merely depressing the foot pedal 22.

The robotic arm assembly 16 includes a linear actuator 24 fixed to the table 14. The linear actuator 24 is connected to a linkage arm assembly 26 and adapted to move the linkage assembly 26 along the z axis of a first coordinate system. As shown in FIG. 2, the first coordinate system also has an x axis and a y axis. The linear actuator 24 preferably has an electric motor which turns a ball screw that moves the output shaft of the actuator.

The linkage arm assembly 26 includes a first linkage arm 28 attached to a first rotary actuator 30 and an end effector 32. The first rotary actuator 30 is adapted to rotate the first linkage arm 28 and end effector 32 in a plane perpendicular to the z axis (x-y plane). The first rotary actuator 30 is connected to a second rotary actuator 34 by a second linkage arm 36. The second actuator 34 is adapted to rotate the first actuator 30 in the x-y plane. The second rotary actuator 34 is connected to a third rotary actuator 38 by a third linkage arm 40. The third rotary actuator 38 is connected to the output shaft of the linear actuator 24 and adapted to rotate the second rotary actuator 34 in the x-y plane. The rotary actuators are preferably electric motors with output shafts attached to the respective linkage arms. The actuators 30, 34 and 38 preferably have gear reduction boxes to increase the torque at the linkage arms relative to the electric motors. The electric motors of the actuators 24, 30, 34 and 38 rotate in response to output signals provided by the computer 20.

Figure 3:
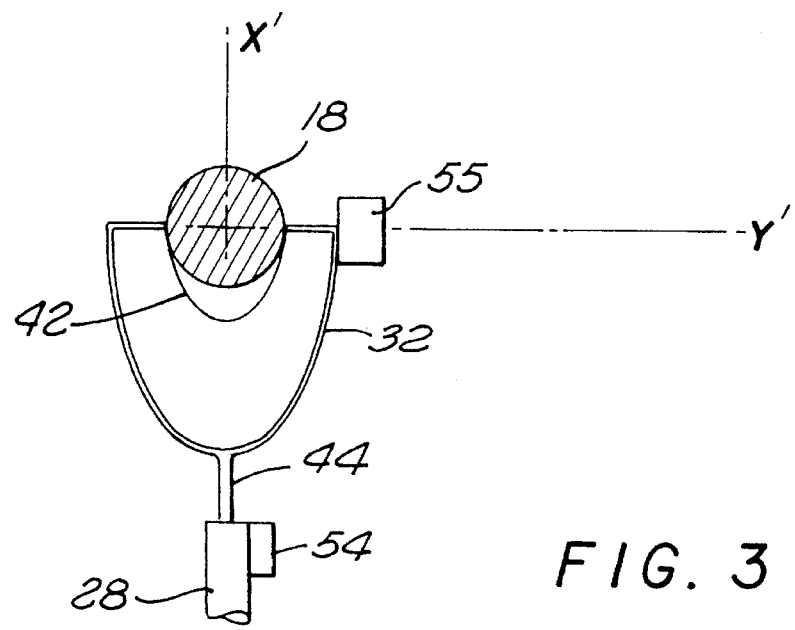
FIG. 3 is a top view of an end effector used to hold an endoscope.

As shown in FIG. 3, the end effector 32 has a clamp 42 which can grasp and hold the endoscope 18. The clamp 42 may be constructed as a wire with a loop that has a diameter smaller than the outside diameter of the scope 18. The clamp 42 allows the scope to be easily attached to and removed from the robotic arm assembly 16. Although a simple wire clamp is shown and described, it is to be understood that the end effector 32 may have any means required to secure the surgical instrument 18. As shown in FIGS. 1 and 2, the junction of the endoscope 18 and the end effector 32 define a second coordinate system which has an x' axis, a y' axis and a z' axis. The end of the endoscope within the patient is located in a third coordinate system which has an x" axis, a y" axis and a z" axis.

The end effector 32 has a shaft 44 which can be coupled to the first linkage arm 28. The first linkage arm 28 may have a bearing which allows the end effector 32 to rotate about the longitudinal axis of the arm 28. The end effector 32 may be constructed so that the clamp 42 and scope 18 can rotate about the y' axis. The end effector 32 is preferably constructed to be detached from the first linkage arm 28, so that a sterile instrument can be used for each surgical procedure. The robotic system 10 may also have a bag or cover to encapsulate the robotic arm assembly 16 to keep the assembly 16 sterile.

The actuators 24, 30, 34 and 38 may each have position sensors 46-52 that are connected to the computer 20. The sensors may be potentiometers that can sense the rotational movement of the electric motors and provide feedback signals to the computer 20. The end effector 32 may also have a first joint position sensor 54 that senses the angular displacement of the effector about the x' axis and a second joint position sensor 55 which senses the angular displace of the scope about the y' axis.

Figure 4:
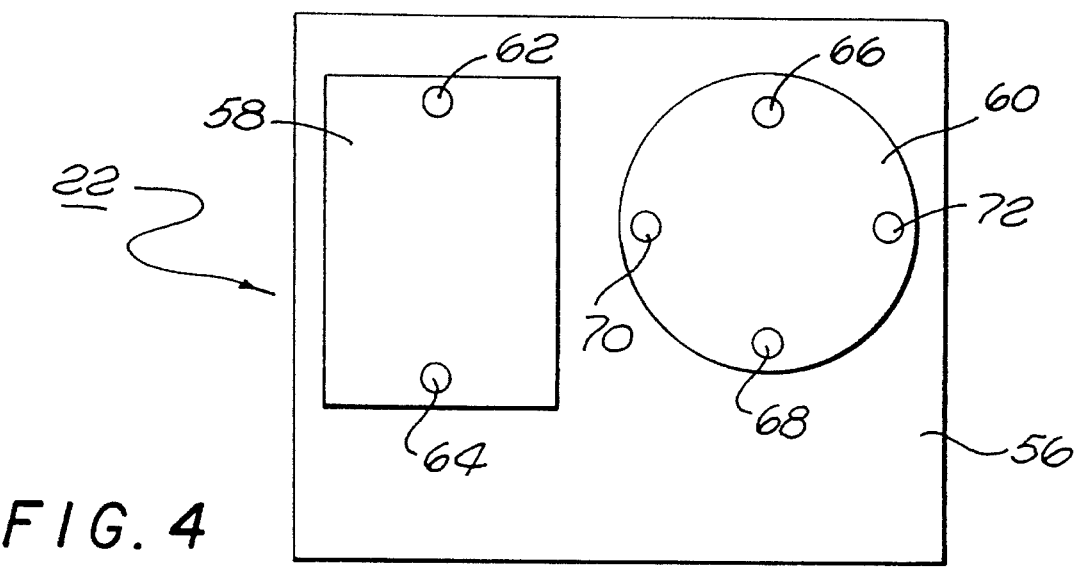
FIG. 4 is a top view of a foot pedal of the system of FIG. 1.
Figure 5:
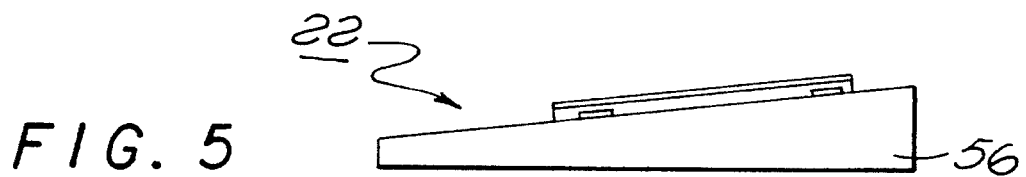
FIG. 5 is a cross-sectional view of the foot pedal of FIG. 4.

FIGS. 4 and 5 show a preferred embodiment of the foot pedal 22. The foot pedal 22 has a housing 56 that supports a first foot switch 58 and a second foot switch 60. The first foot switch 58 has a first pressure transducer 62 and a second pressure transducer 64. The second foot switch 60 has third 66, fourth 68, fifth 70 and sixth 72 pressure transducers. The transducers are each connected to a corresponding operational amplifier that provides a voltage input to the computer 20. The pressure transducers 62-72 are constructed so that the resistance of each transducer decreases as the surgeon increases the pressure on the foot switches. Such a transducer is sold by Interlink Electronics. The decreasing transducer resistance increases the input voltage provided to the computer 20 from the operational amplifier. Each transducer corresponds to a predetermined direction in the third coordinate system. In the preferred embodiment, the first pressure transducer 62 corresponds to moving the endoscope toward the image viewed by the surgeon. The second transducer 64 moves the scope away from the image. The third 66 and fourth 68 transducers move the scope 18 "up" and "down", respectively, and the fifth 70 and sixth 72 transducers move the scope 18 "left" and "right", respectively.

Figure 6:
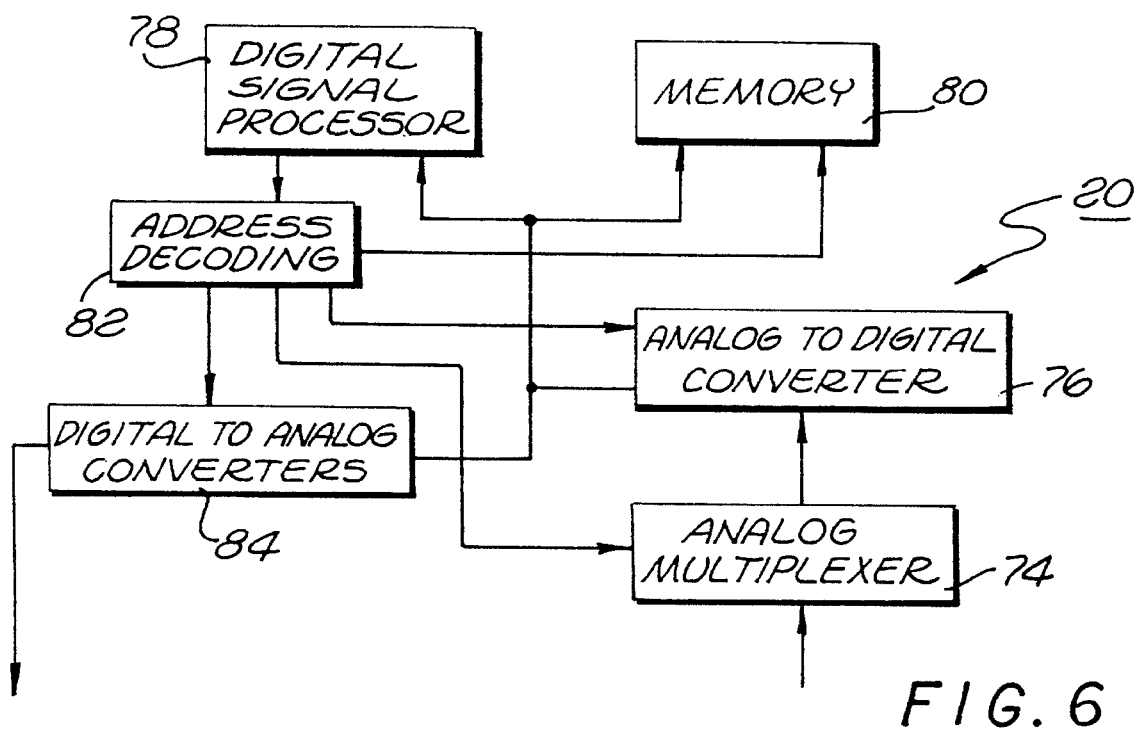
FIG. 6 is a schematic of a computer of the robotic system shown in FIG. 1.

FIG. 6 shows a schematic of the computer 20. The computer 20 has a multiplexer 74 which is connected to the pressure transducers and the position sensors. In the preferred embodiment, the multiplexer 74 has 12 channels, one channel for each sensor and transducer. The multiplexer 74 is connected to a single analog to digital (A/D) converter 76.

The computer also has a processor 78 and memory 80. The A/D converter 76 is constructed so that the converter can provide the processor 78 with a binary string for each voltage level received from the input signals of the system. By way of example, the transducers may provide a voltage ranging between 0-10 volts (V) and the converter 76 may output a different 12 bit binary string for each voltage level. An input signal of 1.0 V may correspond to the binary string 000011001010, 2.0 V may correspond to 000111010100 and so forth and so on.

The processor 78 is connected to an address decoder 82 and four separate digital to analog (D/A) converters 84. Each D/A converter is connected to an actuator 26, 30, 34 or 38. The D/A converters 84 provide analog output signals to the actuators in response to output signals received from the processor 78. The analog output signals preferably have a sufficient voltage level to energize the electric motors and move the robotic arm assembly. The D/A converters 84 may be constructed so that a binary 1 from the processor produces an analog output signal that drives the motors. In such an embodiment, the motors are energized for as long as the processor provides a binary 1 output signal. The decoder 82 correlates the addresses provided by the processor with a corresponding D/A converter, so that the correct motor(s) is driven. The address decoder 82 also provides an address for the input data from the A/D converter so that the data is associated with the correct input channel.

The processor 78 computes the movement of the robotic arm assembly 16 in accordance with the following algorithms.

$$a3 = \pi - \cos^{-1}\left(\frac{(x - L3\cos(\pi))^2 + (y - L3\sin(\pi))^2 - L1^2 - L2^2}{2L1L2}\right) \quad (1)$$

$$\Delta = \cos^{-1}\left(\frac{(x - L3\cos(\pi))^2 + (y - L3\sin(\pi))^2 + L1^2 - L2^2}{2L1\sqrt{(x - L3\cos(\pi))^2 + (y - L3\sin(\pi))^2}}\right)$$

$$a0 = \tan^{-1}2\left(\frac{y - L3\sin(\pi)}{x - L3\sin(\pi)}\right)$$

$$a2 = a0 +/- \Delta$$

$$a4 = \pi - a2 - a3$$

where;
- a2=angle between the third linkage arm and the x axis.
- a3=angle between the second linkage arm and the longitudinal axis of the third linkage arm.
- a4=angle between the first linkage arm and the longitudinal axis of the second linkage arm.
- L1=length of the third linkage arm.
- L2=length of the second linkage arm.
- L3=length of the first linkage arm.
- Π=the angle between the first linkage arm and the x' axis of the second coordinate system.

x=x coordinate of the end effector in the first coordinate system.

y=y coordinate of the end effector in the first coordinate system. To move the end effector to a new location the processor 78 computes the change in angles a2, a3 and a4, and then provides output signals to move the actuators accordingly. The original angular position of the end effector is provided to the processor 78 by the sensors 46–55. The processor moves the linkage arms an angle that corresponds to the difference between the new location and the original location of the end effector. The differential angle Δa2 corresponds to the amount of angular displacement provided by the third actuator 38, the differential angle Δa3 corresponds to the amount of angular displacement provided by the second actuator 34 and the differential angle Δa4 corresponds to the amount of angular displacement provided by the first actuator 30.

To improve the effectiveness of the system 10, the system is constructed so that the movement of the surgical instrument as seen by the surgeon, is always in the same direction as the movement of the foot pedal. Thus when the surgeon presses the foot switch to move the scope up, the scope always appears to move in the up direction. To accomplish this result, the processor 78 converts the desired movement of the end of the endoscope in the third coordinate system to coordinates in the second coordinate system, and then converts the coordinates of the second coordinate system into the coordinates of the first coordinate system.

The desired movement of the endoscope is converted from the third coordinate system to the second coordinate system by using the following transformation matrix;

$$\begin{pmatrix} \Delta x' \\ \Delta y' \\ \Delta z' \end{pmatrix} = \begin{pmatrix} \cos(a6) & 0 & -\sin(a6) \\ -\sin(a5)\sin(a6) & \cos(a5) & -\sin(a5)\cos(a6) \\ \cos(a5)\sin(a6) & \sin(a5) & \cos(a5)\cos(a6) \end{pmatrix} \begin{pmatrix} \Delta x'' \\ \Delta y'' \\ \Delta z'' \end{pmatrix} \quad (2)$$

where;

Δx"=the desired incremental movement of the scope along the x" axis of the third coordinate system.

Δy"=the desired incremental movement of the scope along the y" axis of the third coordinate system.

Δz"=the desired incremental movement of the scope along the z" axis of the third coordinate system.

a5=the angle between the scope and a x'-z' plane the second coordinate system.

a6=the angle between the scope and a y'-z' plane the second coordinate system.

Δ'=the computed incremental movement of the scope along the x' axis of the second coordinate system.

Δy'=the computed incremental movement of the scope along the y' axis of the second coordinate system.

Δz'=the computed incremental movement of the scope along the z' axis of the second coordinate system.

Figure 7:
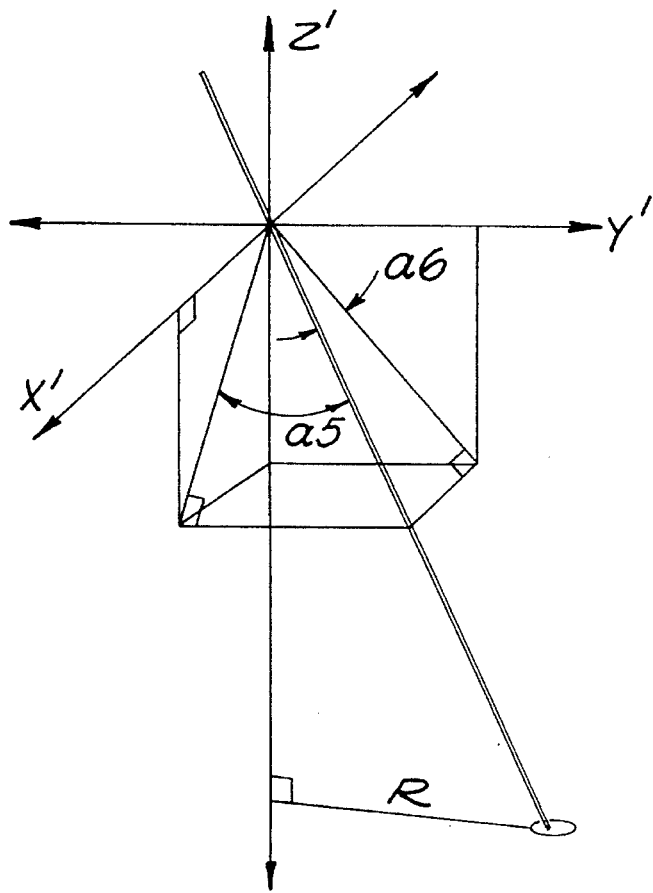
FIG. 7 is a schematic of the endoscope oriented in a second coordinate system.

The angles a5 and a6 are provided by the first 54 and second 55 joint position sensors located on the end effector 32. The angles a5 and a6 are shown in FIG. 7.

The desired movement of the endoscope is converted from the second coordinate system to the first coordinate system by using the following transformation matrix;

$$\begin{pmatrix} \Delta x \\ \Delta y \\ \Delta z \end{pmatrix} = \begin{pmatrix} \cos(\pi) & -\sin(\pi) & 0 \\ \sin(\pi) & \cos(\pi) & 0 \\ 0 & 0 & 1 \end{pmatrix} \begin{pmatrix} \Delta x' \\ \Delta y' \\ \Delta z' \end{pmatrix} \quad (3)$$

where;

Δx'=the computed incremental movement of the scope along the x' axis of the second coordinate system.

Δy'=the computed incremental movement of the scope along the y' axis of the second coordinate system.

Δz'=the computed incremental movement of the scope along the z' axis of the second coordinate system.

Π=is the angle between the first linkage arm and the x axis of the first coordinate system.

Δx=the computed incremental movement of the scope along the x axis of the first coordinate system.

Δy=the computed incremental movement of the scope along the y axis of the first coordinate system.

Δz=the computed incremental movement of the scope along the z axis of the first coordinate system. The incremental movements Δx and Δy are inserted into the algorithms (1) described above for computing the angular movements (Δa2, Δa3 and Δa4) of the robotic arm assembly to determine the amount of rotation that is to be provided by each electric motor. The value Δz is used to determine the amount of linear movement provided by the linear actuator 26.

After each movement of the endoscope a new Π value must be computed. Because the scope is in the y'-z' plane, the Π value only changes when the end effector is moved along the x' axis. The new Π angle is computed with the following algorithms:

$$d = \left| \frac{m}{\tan(a6)} \right| \quad (4)$$

$$r = |d \sin(a5)|$$

$$\Delta \pi = \tan^{-1} \frac{m}{r}$$

where;

d=the length of the endoscope between the end effector and the cannula pivot point.

r=the distance along the y' axis between the end effector and the cannula pivot point.

m=the incremental movement of the scope.

The new Π value is computed and stored in the memory of the computer for further computation.

Figure 8:
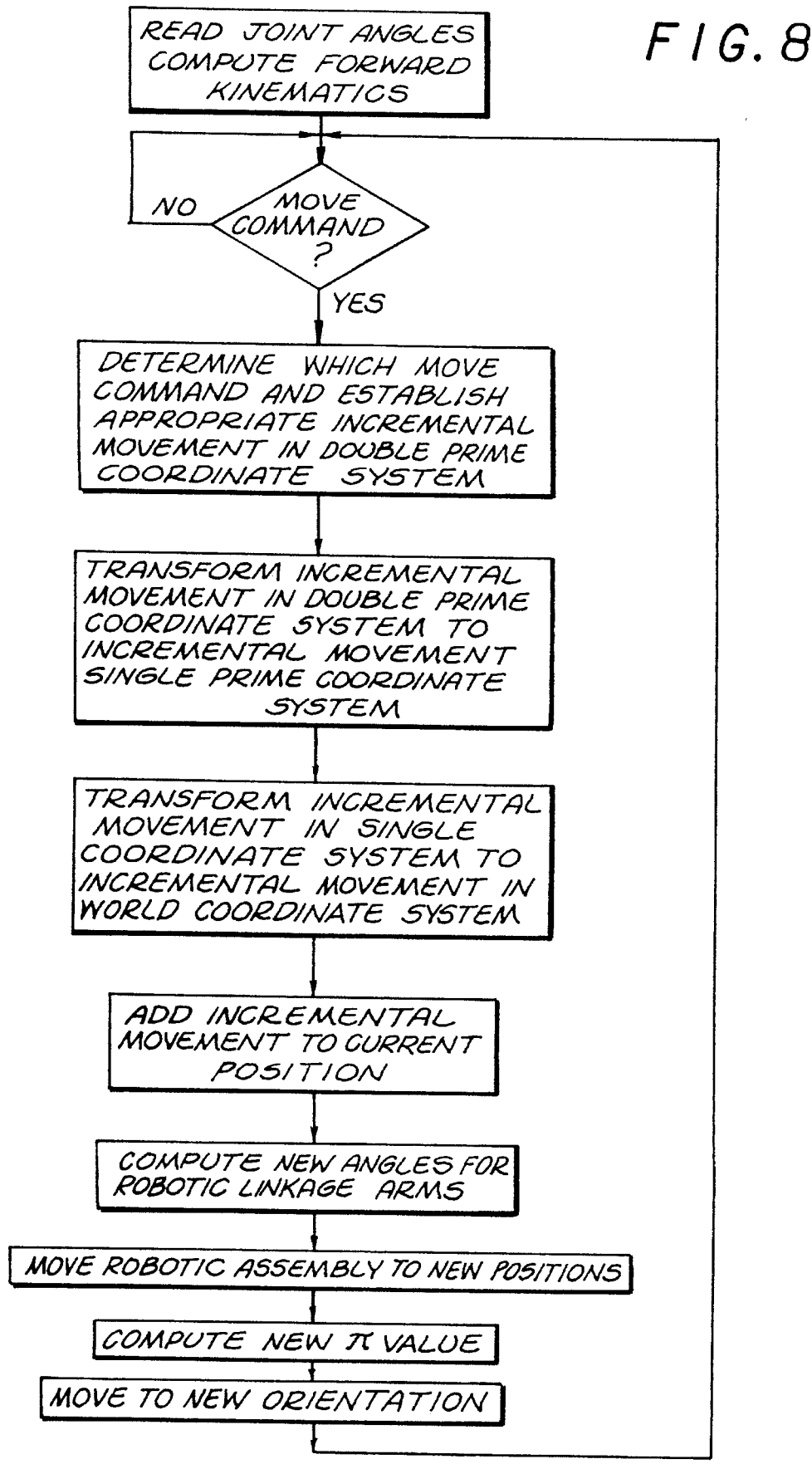
FIG. 8 is a flowchart showing the operation of the system.

FIG. 8 shows a flowchart of a program used to operate the system. The computer 20 initially computes the location of the end effector 32 with the input provided by the sensors 46–55. When the surgeon presses on one of the foot switches, the pedal provides a input signal to the computer. For example, the surgeon may want a closer look at an object in front of the endoscope. The surgeon then presses the top of the first foot switch, depressing the first transducer and providing an input signal to the computer. The input signal is converted into an 12 bit binary string which is received by the processor. The 12 bit string corresponds to a predetermined increment of Δz". The computer is constantly sampling the foot pedal, wherein each sample corresponds to a predetermined increment in the corresponding axis". If the surgeon holds down the foot pedal during two sampling periods then the increment to be moved is 2xΔz". The converter also provides a multiplication factor for each increase in voltage level received from the amplifier of the transducer, so that the increments are increased for each increase in voltage. Thus the surgeon can increase the amount of incremental movement by increasing the pressure on the foot switch.

The processor 78 then computes the coordinates in the second coordinates system. The incremental movements in the third coordinate system ($\Delta x''$, $\Delta y''$ and $\Delta z''$) are used to compute the increment movements in the second coordinate system ($\Delta x'$, $\Delta y'$ and $\Delta z'$) and the coordinates in the first coordinate system ($\Delta x$, $\Delta y$ and $\Delta z$). The incremental movements are then used to determine the change in the angles a2, a3 and a4. The computer provides output signals to the appropriate electric motors to move the robotic arm assembly to the new position. The new Π angle is computed and the process is repeated. The present invention thus allows the surgeon to remotely move a surgical instrument in a manner that directly correlates with the viewing image seen through the endoscope.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for moving an endoscope that is inserted into a patient, comprising the steps of:

a) attaching the endoscope to an end effector of a robotic arm assembly located within a first coordinate system having a first x axis, a first y axis and a first z axis, said robotic arm assembly being adapted to move said end effector relative to the patient in response to an input command from the user, said end effector being located within a second coordinate system having a second x axis, a second y axis and a second z axis;

b) inserting the endoscope into the patient, wherein the end of the endoscope is located within a third coordinate system having a third x axis, a third y axis and a third z axis;

c) inputting a command to move the end of the endoscope an incremental distance in the third coordinate system;

d) computing an incremental moving distance of said end effector in the second coordinate system from the incremental distance of the end of the endoscope in the third coordinate system;

e) computing an incremental moving distance of said end effector within the first coordinate system from the incremental moving distance of said end effector in the second coordinate system; and, moving said robotic arm assembly until said end effector has moved the computed incremental moving distance in the first coordinate system.

2. The method as recited in claim 1, wherein said incremental movement of said end effector in said second coordinate system is computed in accordance with the following transformation matrix:

$$\begin{pmatrix} \Delta x' \\ \Delta y' \\ \Delta z' \end{pmatrix} = \begin{pmatrix} \cos(a6) & 0 & -\sin(a6) \\ -\sin(a5)\sin(a6) & \cos(a5) & -\sin(a5)\cos(a6) \\ \cos(a5)\sin(a6) & \sin(a5) & \cos(a5)\cos(a6) \end{pmatrix} \begin{pmatrix} \Delta x'' \\ \Delta y'' \\ \Delta z'' \end{pmatrix}$$

wherein;

$\Delta x''$=an incremental movement of the end of the endoscope along the third x axis;

$\Delta y''$=an incremental movement of the end of the endoscope along the third y axis;

$\Delta z''$=an incremental movement of the end of the endoscope along the third z axis;

a5=an angle of the endoscope and a second x–z plane in the second coordinate system;

a6=an angle of the endoscope and a second y–z plane in the second coordinate system;

$\Delta x'$=a computed incremental movement of said end effector along the second x axis;

$\Delta y'$=a computed incremental movement of said end effector along the second y axis;

$\Delta z'$=a computed incremental movement of said end effector along the second z axis.

3. The method as recited in claim 2, wherein said incremental movement of said end effector in said first coordinate system is computed in accordance with the following transformation matrix:

$$\begin{pmatrix} \Delta x \\ \Delta y \\ \Delta z \end{pmatrix} = \begin{pmatrix} \cos(\pi) & -\sin(\pi) & 0 \\ \sin(\pi) & \cos(\pi) & 0 \\ 0 & 0 & 1 \end{pmatrix} \begin{pmatrix} \Delta x' \\ \Delta y' \\ \Delta z' \end{pmatrix}$$

wherein;

$\Delta x$=a computed incremental movement of said end effector along the first x axis;

$\Delta y$=a computed incremental movement of said end effector along the first y axis;

$\Delta z$=a computed incremental movement of said end effector along the first z axis;

Π=an angle between said end effector and the first x axis.

4. A method for moving an endoscope that is inserted into a patient, comprising the steps of:

a) attaching the endoscope to an end effector of a robotic arm assembly located within a first coordinate system having a first x axis, a first y axis and a first z axis, said robotic arm assembly having an end effector that is located within a second coordinate system having a second x axis, a second y axis and a second z axis, said robotic arm assembly having a first actuator coupled to said end effector by a first linkage arm, a second actuator coupled to said first actuator by a second linkage arm and a third actuator coupled to said second actuator by a third linkage arm, said actuators being adapted to move said end effector in a plane perpendicular to the first z axis, said robotic assembly further having a linear actuator coupled to said third actuator to move said third actuator along the first z axis;

b) inserting the endoscope into the patient, wherein the end of the endoscope is located within third coordinate system having a third x axis, a third y axis and a third z axis;

c) inputting a command to move the end of the endoscope an incremental distance in the third coordinate system;

d) computing an incremental moving distance of said end effector within the second coordinate system from the incremental moving distance of the end of the endoscope in the third coordinate system;

e) computing an incremental moving distance of said end effector within the first coordinate system from the incremental moving distance of said end effector in the second coordinate system;

f) moving said robotic arm assembly until said end effector has moved the incremental moving distance in the first coordinate system.

5. The method as recited in claim 4, wherein said incremental movements of said end effector in said second coordinate system is computed in accordance with the following transformation matrix:

$$\begin{pmatrix} \Delta x' \\ \Delta y' \\ \Delta z' \end{pmatrix} = \begin{pmatrix} \cos(a6) & 0 & -\sin(a6) \\ -\sin(a5)\sin(a6) & \cos(a5) & -\sin(a5)\cos(a6) \\ \cos(a5)\sin(a6) & \sin(a5) & \cos(a5)\cos(a6) \end{pmatrix} \begin{pmatrix} \Delta x'' \\ \Delta y'' \\ \Delta z'' \end{pmatrix}$$

wherein $\Delta x''$=an incremental movement of the end of the endoscope along the third x axis;

$\Delta y''$=an incremental movement of the end of the endoscope along the third y axis;

$\Delta z''$=an incremental movement of the end of the endoscope along the third z axis;

a5=an angle of the endoscope and a x–y plane in the second coordinate system;

a6=an angle of the endoscope and a y–z plane in the second coordinate system;

$\Delta x'$=a computed incremental movement of said end effector along the second x axis;

$\Delta y'$=a computed incremental movement of said end effector along the second y axis;

$\Delta z'$=a computed incremental movement of said end effector along the second z axis.

6. The method as recited in claim 5, wherein said incremental movement of said end effector in the first coordinate system is computed in accordance with the following information matrix:

$$\begin{pmatrix} \Delta x \\ \Delta y \\ \Delta z \end{pmatrix} = \begin{pmatrix} \cos(\pi) & -\sin(\pi) & 0 \\ \sin(\pi) & \cos(\pi) & 0 \\ 0 & 0 & 1 \end{pmatrix} \begin{pmatrix} \Delta x' \\ \Delta y' \\ \Delta z' \end{pmatrix}$$

wherein;

$\Delta x$=a computed incremental movement of said end effector along the first x axis;

$\Delta y$=a computed incremental movement of said end effector along the first y axis;

$\Delta z$=a computed incremental movement of said end effector along the first z axis;

$\Pi$=an angle between said end effector and the first x axis.

7. The method as recited in claim 6, wherein said linear actuator translates said third actuator $\Delta Z$, said third actuator rotates said third linkage arm an angle of $\Delta a2$, wherein a2 is computed by the equations;

$$\Delta = \cos^{-1}\left( \frac{(x - L3\cos(\pi))^2 + (y - L3\sin(\pi))^2 + L1^2 - L2^2}{2L1 \sqrt{(x - L3\cos(\pi))^2 + (y - L3\sin(\pi))^2}} \right)$$

$$a0 = \tan^{-1}2\left( \frac{y - L3\sin(\pi)}{x - L3\sin(\pi)} \right)$$

$$\Delta a2 = a0 +/- \Delta$$

said second actuator rotates said second linkage arm an angle $\Delta a3$ wherein $\Delta a3$ is computed by the equation;

$$\Delta a3 = \pi - \cos^{-1}\left( \frac{(x - L3\cos(\pi))^2 + (y - L3\sin(\pi))^2 - L1^2 - L2^2}{2L1L2} \right)$$

wherein;

L1=is a length of said third linkage arm;

L2=is a length of said second linkage arm;

L3=is a length of said third first arm;

and said first actuator rotates said first linkage arm an angle $\Delta a4$ wherein $\Delta a4$ is computed by the equation:

$$\Delta a4 = \pi - \Delta a2 - \Delta a3.$$

* * * * *